US00PP34766P3

(12) United States Plant Patent

Mukai et al.

(10) Patent No.: US PP34,766 P3
(45) Date of Patent: Nov. 22, 2022

(54) *SALVIA* PLANT NAMED 'TL966'

(50) Latin Name: *Salvia hybrida*
Varietal Denomination: TL966

(71) Applicant: TAKII & Co., Ltd., Kyoto (JP)

(72) Inventors: Yutaka Mukai, Kyoto (JP); Shun Koyama, Kyoto (JP)

(73) Assignee: TAKII & Co. Ltd., Kyoto (JP)

( * ) Notice: Subject to any disclaimer, the term of this patent is extended or adjusted under 35 U.S.C. 154(b) by 0 days.

(21) Appl. No.: 17/562,946

(22) Filed: Dec. 27, 2021

(65) Prior Publication Data

US 2022/0225554 P1 Jul. 14, 2022

Related U.S. Application Data

(60) Provisional application No. 63/136,409, filed on Jan. 12, 2021.

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 5/02
See application file for complete search history.

(56) References Cited

PUBLICATIONS https://www.mandycanudigit.com/2019/12/05/new-alstroemeria-dahlia-and-salvia-from-thompson-morgan/?doing_wp_cron=1644254864.8831019401550292968750; Dec. 5, 2019; 2 pages.*
https://www.hilverdaflorist.com/assortment/product/strawberry-lake/ ; Feb. 7, 2022; 1 page.*

* cited by examiner

*Primary Examiner* — Kent L Bell
(74) *Attorney, Agent, or Firm* — C. Anne Whealy

(57) ABSTRACT

A new and distinct cultivar of *Salvia* plant named 'TL966', characterized by its upright to outward plant habit; strong and vigorous growth habit; freely branching habit; strong and healthy roots and leaves; uniform and freely flowering habit; strong and upright inflorescences with numerous reddish purple-colored flowers; and good garden performance.

1 Drawing Sheet

Botanical designation: *Salvia hybrida.*
Cultivar denomination: 'TL966'.

STATEMENT REGARDING PRIOR DISCLOSURES BY INVENTOR & APPLICANT

An European Community Plant Breeder's Rights application for the instant plant was filed by the Applicant, Takii & Co., Ltd. of Kyoto, Japan on Dec. 11, 2020, application number 2020/3272. Foreign priority is not claimed to this application.

The Inventor & Applicant assert that no publications nor advertisements relating to sales, offers for sale or public distribution occurred more than one year prior to the effective filing date of this application. Any information about the claimed plant would have been obtained from a direct or indirect disclosure from the Inventor or the Applicant. Inventor & Applicant claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Salvia* plant, botanically known as *Salvia hybrida* and hereinafter referred to by the name 'TL966'.

The new *Salvia* plant is a product of a planned breeding program conducted by the Inventors in Kyoto, Japan. The objective of the breeding program is to develop new strong and freely flowering *Salvia* plants with attractive inflorescences and good garden performance.

The new *Salvia* plant originated from a cross-pollination in May, 2014 in Kyoto, Japan of a proprietary selection of *Salvia hybrida* identified as code number 12,228, not patented, as the female, or seed, parent with a proprietary selection of *Salvia hybrida* identified as code number 12,4157, not patented, as the male, or pollen, parent. The new *Echinacea* plant was discovered and selected by the Inventors as a single flowering plant from within the progeny of the stated cross-pollination grown in a controlled greenhouse environment in Kyoto, Japan on Mar. 15, 2015.

Asexual reproduction of the new *Salvia* plant by terminal cuttings in Kyoto, Japan since September, 2015 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'TL966'. These characteristics in combination distinguish 'TL966' as a new and distinct cultivar of *Salvia:*

1. Upright to outward plant habit.
2. Strong and vigorous growth habit.
3. Freely branching habit.
4. Strong and healthy roots and leaves.
5. Uniform and freely flowering habit.
6. Strong and upright inflorescences with numerous reddish purple-colored flowers.
7. Good garden performance.

Plants of the new *Salvia* can be compared to plants of the female parent selection. Plants of the new *Salvia* differ primarily from plants of the female parent selection in the following characteristics:

1. Plants of the new *Salvia* are taller than plants of the female parent selection.
2. Plants of the new *Salvia* are more freely branching than plants of the female parent selection.
3 Plants of the new *Salvia* have reddish purple-colored flowers whereas plants of the female parent selection have purple-colored flowers.

Plants of the new *Salvia* can be compared to plants of the male parent selection. Plants of the new *Salvia* differ primarily from plants of the male parent selection in the following characteristics:

1. Plants of the new *Salvia* flower two weeks earlier than plants of the male parent selection.
2. Plants of the new *Salvia* have longer inflorescences than plants of the male parent selection.
3 Plants of the new *Salvia* have larger flowers than plants of the male parent selection.

Plants of the new *Salvia* can be compared to plants of 'TL 993', not patented. In side-by-side comparisons, plants of the new *Salvia* differ from plants of 'TL 993' in the following characteristics:

1. Plants of the new *Salvia* are taller than plants of 'TL 993'.
2. Plants of the new *Salvia* have larger leaves than plants of 'TL 993'.
3 Flowers of plants of the new *Salvia* are darker reddish purple in color than flowers of plants of 'TL 993'.

BRIEF DESCRIPTION OF THE PHOTOGRAPH

The accompanying colored photograph illustrates the overall appearance of the new *Salvia* plant, showing the colors as true as it is reasonably possible to obtain in colored reproductions of this type. Colors in the photograph may differ slightly from the color values cited in the detailed botanical description which accurately describe the actual colors of the new *Salvia* plant.

The photograph is a side perspective view of a typical flowering plant of 'TL966' grown in a container.

DETAILED BOTANICAL DESCRIPTION

The aforementioned photograph and following observations and measurements describe plants grown during the spring and early summer in 15-cm containers in a glass-covered greenhouse and "finished" in an outdoor nursery in De Kwakel, The Netherlands under cultural practices typically used in commercial *Salvia* production. During the production of the plants, greenhouse day temperatures averaged 20° C., outdoor nursery day temperatures ranged from 10° C. to 15° and greenhouse and outdoor nursery night temperatures ranged from 14° C. to 15° C. Plants were 25 weeks from planting when the photograph was taken and 20 weeks from planting when the description was taken. In the following description, color references are made to The Royal Horticultural Society Colour Chart, 2015 Edition, except where general terms of ordinary dictionary significance are used.

Botanical classification: *Salvia hybrida* 'TL966'.

Parentage:

*Female, or seed, parent.*—Proprietary selection of *Salvia hybrida* identified as code number 12,228, not patented.

*Male, or pollen, parent.*—Proprietary selection of *Salvia hybrida* identified as code number 12,4157, not patented.

Propagation:

*Type.*—By terminal cuttings.

*Time to initiate roots, summer.*—About seven days at temperatures about 20° C.

*Time to initiate roots, winter.*—About ten days at temperatures about 20° C.

*Time to produce a rooted young plant, summer.*—About 27 days at temperatures about 20° C.

*Time to produce a rooted young plant, winter.*—About 35 days at temperatures about 20° C.

*Root description.*—Medium in thickness, somewhat fibrous; typically greyed white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial typically grown as a container and garden plant; upright to outward plant habit; vigorous growth habit and moderate to rapid growth rate.

*Branching habit.*—Freely branching habit with about six primary lateral branches each with about four secondary lateral branches developing per plant; pinching is not required, but will improve branching and flowering potential.

*Plant height, soil level to top of foliar plane.*—About 45.6 cm.

*Plant height, soil level to top of floral plane.*—About 60.2 cm.

*Plant width.*—About 45.5 cm.

*Primary branch description.*—Length: About 32.8 cm. Diameter: About 8 mm. Internode length: About 6.9 cm. Shape: Quadrangular. Strength: Strong. Branch angle: Erect to about 60° from vertical. Texture and luster: Moderately pubescent; slightly glossy. Color, developing: Close to 143B and tinged with close to 176A to 177A. Color, developed: Close to 143A and 144A; at the internodes, close to 146A, 148A, 152A and 152B tinged with close to 176C and 176D.

Leaf description:

*Arrangement.*—Opposite; simple.

*Length.*—About 8.2 cm.

*Width.*—About 5.9 cm.

*Shape.*—Deltoid.

*Apex.*—Apiculate.

*Base.*—Short attenuate.

*Margin.*—Serrate.

*Texture and luster, upper surface.*—Moderately pubescent; slightly rugose; slightly glossy.

*Texture and luster, lower surface.*—Mostly glabrous except for venation which is moderately pubescent; slightly rugose; matte.

*Venation pattern.*—Pinnate.

*Color.*—Developing leaves, upper surface: Close to 137A. Developing leaves, lower surface: Close to a blend of 138A and 147B. Fully expanded leaves, upper surface: Darker than a blend of close to 139A and 147A; venation, close to 152C to 152D. Fully expanded leaves, lower surface: Close to 147B; venation, close to 146B and proximally, close to 152A.

*Petioles.*—Length: About 5.1 cm. Diameter: About 2 mm. Strength: Moderately strong. Texture and luster, upper surface: Moderately pubescent; slightly glossy. Texture and luster, lower surface: Smooth, glabrous; moderately glossy. Color, upper surface: Close to 148B; at the margins, close to a blend of between 152A and N199A. Color, lower surface: Close to 146B.

Flower description:

*Flower arrangement and shape.*—Single bilabiate flowers arranged on long terminal verticillasters; flowers face mostly outwardly.

*Flowering habit.*—Freely flowering habit, about 80 flowers per inflorescence and about 800 flowers per plant develop during the flowering season.

*Natural flowering season.*—Continuous flowering from the late spring into the summer in The Netherlands; plants begin flowering about 14 weeks from unrooted cuttings.

*Flower longevity on the plant.*—About ten days; flowers not persistent.

*Fragrance.*—None detected; stems and leaves, however, are aromatic.

*Flower buds.*—Length: About 1.9 cm. Diameter: About 8 mm. Shape: Obovate. Texture and luster: Moderately to densely pubescent; matte. Color: Sepals, close to 176A to 176B and proximally, close to 166B; petals, close to N79C.

*Inflorescence length.*—About 28.4 cm.

*Inflorescence diameter.*—About 10.5 cm.

*Flower diameter.*—About 1.6 cm by 2.2 cm.

*Flower length (depth).*—About 5.4 mm.

*Flower throat diameter.*—About 3 mm by 7 mm.

*Flower tube length.*—About 3.2 cm.

*Flower tube diameter.*—About 5 mm by 1 cm.

*Petals.*—Arrangement: Five petals with two upper petals fused forming a galea and three lower petals fused forming a broader lower protruding lip. Galea length: About 1.5 cm. Galea width: About 4 mm. Lower lip length: About 1 cm. Lower lip width: About 1.6 cm. Galea shape: Oblanceolate, folded. Lower lip shape: Reniform. Galea apex: Emarginate. Lower lip apex: Tri-lobed, lobes obtuse. Galea and lower lip base: Fused. Margin: Entire; galea, not undulate and lower lip, slightly undulate with center lobe, reflexed. Galea and lower lip, texture and luster, upper surface: Smooth, glabrous; slightly velvety; matte. Galea and lower lip, texture and luster, lower surface: Galea, densely pubescent and lower lip, sparsely pubescent; matte. Throat, texture and luster: Smooth, glabrous; slightly velvety; matte. Tube, texture and luster: Densely pubescent; matte. Color, galea: When opening, upper surface: Close to NN74B. When opening, lower surface: Close to NN78A. Fully opened, upper surface: Close to a blend of N78B and NN78B; venation, similar to lamina color; color does not change with subsequent development. Fully opened, lower surface: Slightly lighter than N79C; venation, similar to lamina color; color does not change with subsequent development. Color, lower lip: When opening, upper surface: Close to NN78C. When opening, lower surface: Close to NN74C. Fully opened, upper surface: Close to NN78B to NN78C; venation, similar to lamina color; color does not change with subsequent development. Fully opened, lower surface: Close to NN78B to NN78C; venation, similar to lamina color; color does not change with subsequent development. Color, throat: Close to N80D; venation, close to N80D. Color, tube: Close to a blend of N78A and N79C and towards the base, close to N78B; venation, similar to lamina color.

*Calyx.*—Arrangement: Two fused sepals to form a campanulate calyx; lower 60% of calyx is fused. Calyx length: About 2 cm. Calyx diameter: About 9 mm. Sepal length: About 2 cm. Sepal width: About 1 cm. Sepal shape: Obovate. Sepal apex: Upper sepal, apiculate and lower sepal, emarginate. Sepal margin: Entire. Sepal texture and luster, inner surface: Smooth, glabrous; matte. Texture and luster, outer surface: Mostly glabrous except for venation which is moderately pubescent; matte. Color: When developing, inner surface: Close to 176A and towards the base, close to 147C. When developing, outer surface: Close to 176A to 176B and towards the base, close to 166B. Fully developed, inner surface: Close to 176A and towards the base, close to 147C. Fully developed, outer surface: Slightly darker than close to a blend of 177A and 178A.

*Peduncles.*—Length: About 27.5 cm. Diameter: About 3.5 mm. Strength: Strong. Aspect: Mostly erect to arching slightly outwardly. Texture and luster: Moderately pubescent; matte. Color: Close to 172B; axillary peduncles with stripes, close to 146A.

*Pedicels.*—Length: About 5 mm. Diameter: About 1 mm. Strength: Moderately strong. Aspect: About 70° from peduncle axis. Texture and luster: Densely pubescent; matte. Color: Close to 166A.

*Reproductive organs.*—Stamens: Quantity per flower: Two. Filament length: About 1.6 cm. Filament color: Close to 77D and proximally, close to 70B. Anther size: About 1 mm by 4 mm. Anther shape: Narrowly oblong. Anther color: Close to 182D with margins, close to N186C. Pollen amount: Scarce. Pollen color: Close to 158D. Pistils: Quantity per flower: One. Pistil length: About 5 cm. Stigma diameter: About 4 mm. Stigma shape: Cleft. Stigma color: Close to N79A. Style length: About 4.9 cm. Style color: Close to 77A and towards the base, close to N155B. Ovary color: Close to 145A.

*Flower bracts.*—Quantity and arrangement: One, at the base of the flower. Length: About 9 mm. Width: About 6 mm. Shape: Broadly ovate. Margin: Entire. Texture and luster, upper and lower surfaces: Smooth, glabrous; matte. Color, upper surface: Close to 178A and towards the base, close to 195B. Color, lower surface: Close to 166A.

*Seeds and fruits.*—To date, seed and fruit production has not been observed on plants of the new *Salvia.*

Pathogen & pest resistance: To date, plants of the new *Salvia* have not been noted to be resistant to pathogens and pests common to *Salvia.*

Garden performance: Plants of the new *Salvia* have exhibited good tolerance to rain, wind and temperatures ranging from −5° C. to 40° C. and to be suitable for USDA Hardiness Zones 9 to 12.

It is claimed:

1. A new and distinct *Salvia* plant named 'TL966' as illustrated and described.

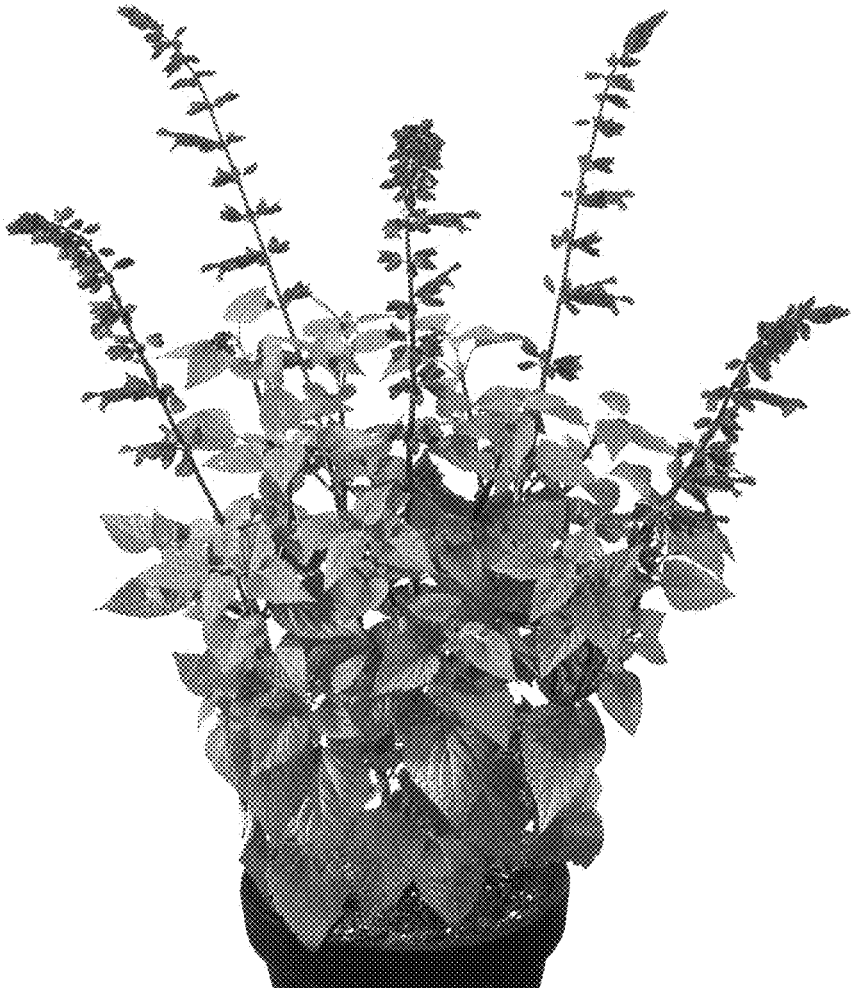

* * * * *